United States Patent
Tojo (10) Patent No.: US 7,186,974 B2
(45) Date of Patent: Mar. 6, 2007

(54) ELECTROSPRAY EMITTER COATED WITH MATERIAL OF LOW SURFACE ENERGY

(76) Inventor: Hiromasa Tojo, 1-88-305 Koyoen-Sanno-cho, Nishinomiya (JP) 662-0018

( * ) Notice: Subject to any disclaimer, the term of this patent is extended or adjusted under 35 U.S.C. 154(b) by 0 days.

(21) Appl. No.: 11/219,009

(22) Filed: Sep. 2, 2005

(65) Prior Publication Data

US 2006/0022131 A1 Feb. 2, 2006

(30) Foreign Application Priority Data

Mar. 3, 2004 (WO) .................... PCT/JP04/02683

(51) Int. Cl.
*H01J 49/00* (2006.01)
*B01D 59/44* (2006.01)

(52) U.S. Cl. .................... 250/288; 250/281; 250/282

(58) Field of Classification Search .................... None
See application file for complete search history.

(56) References Cited

U.S. PATENT DOCUMENTS 6,397,838 B1 * 6/2002 Zimlich et al. ........ 128/200.14
6,796,303 B2 * 9/2004 Zimlich et al. ........ 128/200.14

2001/0001452 A1 5/2001 Davis

FOREIGN PATENT DOCUMENTS

| EP | 0 566 022 | 10/1993 |
|---|---|---|
| EP | 1 254 725 | 11/2002 |
| WO | WO 01/50820 | 7/2001 |
| WO | WO 01/94907 | 12/2001 |
| WO | WO 02/30486 | 4/2002 |

* cited by examiner

*Primary Examiner*—Nikita Wells
(74) *Attorney, Agent, or Firm*—Heisler & Associates

(57) ABSTRACT

This invention relates to an electrospray emitter which comprises an emitter body comprising an inlet orifice, an outlet orifice and a channel connecting the inlet orifice and the outlet orifice; and a coating formed at least on the outer surface of the exit end of the emitter body with a material of low surface energy. The emitters can produce stable electrospray without the aid of any nebulizing gas in the flow rate range of micro-to nano-liters, depending on the surface tension of solvent including distilled water with a high surface tension. The electrically non-conductive nature of their tips virtually eliminates electrical discharge and allows stable electrospray in the negative ion mode. To prevent loss of analytes during delivery between the emitter and analytical devices, e.g., liquid chromatography, a method of coating the inner surface of the connecting line with chemically inert material of low surface energy is also described.

15 Claims, 10 Drawing Sheets

ELECTROSPRAY EMITTER COATED WITH MATERIAL OF LOW SURFACE ENERGY

CROSS-REFERENCE TO RELATED APPLICATIONS

This application claims benefit of the earlier filing dates associated with International Application No. PCT/JP2004/002683 filed on Mar. 3, 2004, which designates the United States and other countries; and U.S. Provisional Application No. 60/452,593 filed on Mar. 4, 2003 which was claimed for priority in the above-identified international application.

FIELD OF THE INVENTION

This invention generally relates to electrospray emitters, methods of preparing such emitters, tubular connectors for connecting electrospray emitters with analytical devices, and use thereof.

BACKGROUND OF THE INVENTION

Electrospray ionization (ESI) mass spectrometry (MS) is now widely used for analyses of biomolecules, pharmaceutical compounds, synthetic polymers and so on (N. Ceck, et al., Mass Spectrom. Rev. 2001, 20, 362–387). Great needs to enhanced sensitivity and better connectivity for capillary high-performance liquid chromatography (HPLC), especially in proteomics and metabolomics, have led to ESI operation in the low flow rate range of less than 1 μl/min. This was achieved using tapered capillary emitters with a very small outlet orifice, usually made of glass and fused silica with or without either metal or conducting-polymer coating, and of stainless steel (D. Gale, et al., Rapid Commun. Mass Spectrom. 1993, 7, 1017–1021; M. Emmett, et al., J. Am. Soc. Mass Spectrom. 1994, 5, 605–613; G. Valaskovic, et al., Anal. Chem. 1995, 67, 3802–3805; M. Wilm, et al., Anal. Chem. 1996, 68, 1–8; E. Maziarz III, et al., J. Am. Soc. Mass Spectrom. 2000, 11, 659–663; and Y. Ishihama, et al., Rapid Commun. Mass Spectrom. 2002, 16, 913–918). Practice with these emitters have, however, revealed problems, such as, easy clogging at their exit orifices, and instability of spraying water-rich solution of a high surface tension at an early stage of gradient elution on reverse-phase HPLC being frequently used for proteomics and metabolomics.

These problems are mutually related and arise primarily from the high surface energy ($\gamma L$ and $\gamma S$, respectively) of both aqueous solutions and materials the emitters are made of. Electrospray initiates from expansion of liquid into a dynamic cone with the charged surface (Taylor cone) at the capillary exit by the applied high electric field (for review ref. 1 and references cited therein). When the force of the applied field on and Coulombic repulsion of the surface charges surpass the surface tension of solution, droplets with excess charge of a given sign detach from the cone. Higher surface energy of the tip material ($\gamma S$=about 100 mN/m for glass) produces a cone supported by the base of a larger diameter on the outer wall of the tip (FIG. 1A), leading to a lower charge density on the cone surface, because the rate of excess charge production at the electric contact site of the emitter is rather constant. This causes difficulty in spraying aqueous solutions of the high surface tension ($\gamma L$=73 mN/m), and eventually a need to extremely sharp emitter tips.

SUMMARY OF THE INVENTION

In view of the above circumstances, the inventor made intensive studies, and found that these problems can be circumvented by coating at least the exit ends of emitters with material of low surface energy.

Accordingly, the present invention provides an electrospray emitter which comprises an emitter body comprising an inlet orifice, an outlet orifice and a channel connecting the inlet orifice and the outlet orifice; and a coating formed at least on the outer surface of the exit end of the emitter body with a material of low surface energy. Suitable materials of low surface energy include, for example, a fluoropolymer such as perfluoropolyoxetane (hereafter referred to as "PFPO"). The emitter body may be made of fused-silica, glass ceramics, aluminosilicate glass, polypropyrene, or stainless steel. The emitter body is preferably tapered toward the outlet orifice. The inner wall of the emitter body may also be coated with the material of low surface energy.

Another aspect of the present invention relates to a method for making an electrospray emitter, which comprises: providing an electrospray emitter comprising an emitter body having an inlet orifice, an outlet orifice and a channel connecting the inlet orifice and the outlet orifice; and forming a coating with a material of low surface energy at least on the outer surface of the exit end of the emitter body.

According to the present invention, the emitters can produce stable electrospray of solutions with a variety of surface tensions including distilled water of a high surface tension without the aid of any nebulizing gas in the flow rate range of micro- to nano-liters. The electrically non-conductive nature of their tips virtually eliminates electrical discharge and allows stable electrospray in the negative ion mode. Further, the electrospray emitter of the present invention can show remarkably improved durability because (1) the exit tip can be made broader as compared with conventional emitters because of improved spray efficiency; and (2) non-specific adhesion can be prevented by inner coating of the emitter body. Therefore, the electrospray emitter of the present invention can be made extremely durable, and thus can be used for 500 hours or more. To prevent loss of analytes in tubular connectors or channels for connecting between the emitter and analytical devices (e.g., liquid chromatography, capillary electrophoresis, supercritical fluid chromatography, and microfabricated channels on a microfluidic device), the inner wall of the tubular connector is coated with a material of low surface energy.

Accordingly, yet another aspect of the present invention relates to a tubular connector for connecting an electrospray emitter and an analytical device, which comprises a tubular connector body comprising an inlet orifice, an outlet orifice and a passage communicating between the inlet orifice and the outlet orifice; and a coating formed on at least a portion of the inner surface of the connector body with a material with low surface energy. Preferably, the inner surface of the connector body is entirely coated with a material with low surface energy. Suitable materials with low surface energy are as described above. The use of the tubular connector of the present invention can improve the recovery of hydrophobic analytes.

OBJECTS OF THE INVENTION

According to the present invention, the emitters can produce stable electrospray without the aid of any nebulizing gas in the flow rate range of micro- to nano-liters, depending on the surface tension of solvent including distilled water with a high surface tension. The electrically non-conductive nature of their tips virtually eliminates electrical discharge and allows stable electrospray in the negative ion mode. These characteristics of the emitters are compatible with high-throughput reverse phase HPLC using water-rich solvent in the early phase of gradient elution on proteomics and metabolomics, and studies using intact proteins in purely aqueous solutions. The latter includes protein-protein interaction, protein-ligand interaction, protein conformational changes, and protein folding-unfolding equilibrium. In addition, the present emitters is applicable to MS analyses of whole proteins using ultra-high resolution Fourier transform ion cyclotron resonance MS in the absence of organic solvents that can assist ESI by conventional emitters, but cause protein precipitations. The capability of the emitters of the present invention in the negative ion modes facilitates ESI-MS application to metabolomics (S. Takagi, et al., J. Clin. Invest 2003, 112, 1372–1382) and pharmacological profilings.

The present invention also provides a tubular connector (capillary, tubing, connecting line) for connecting an electrospray emitter and an analytical device, which can prevent sample losses. The coating with a material of low surface energy in this invention is applicable to the micro-channels of microfluidic devices as well as the channels of liquid-delivering connectors between analytical devices.

The present invention can be practiced based on the above description, however, for reference purposes, the following references are incorporated herein.

1. Ceck, N. B.; Enke, C. G. Practical implications of some recent studies in electrospray ionization fundamentals. Mass Spectrom. Rev. 2001, 20, 362–387.

2. Gale, D. C.; Smith, R. D. Small volume and low flow-rate electrospray ionization mass spectrometry of aqueous samples. Rapid Commun. Mass Spectrom. 1993, 7, 1017–1021.

3. Emmett, M. R.; Caprioli, R. M. Micro-electrospray mass spectrometry: ultra-high-sensitivity analysis of peptides and proteins. J. Am. Soc. Mass Spectrom. 1994, 5, 605–613.

4. Valaskovic, G. A.; Kelleher, N. L.; Little, D. P.; Aaserud, D. J. McLafferty, F. W. Attomole-sensitivity electrospray source for large-molecule mass spectrometry. Anal. Chem. 1995, 67, 3802–3805.

5. Wilm, M.; Mann, M. Analytical properties of the nanoelectrospray ion source. Anal. Chem. 1996, 68, 1–8.

6. Maziarz III, E. P.; Lorenz, S. A.; White, T. P.; Wood, T. D. Polyaniline: A conductive polymer coating for durable nanospray emitters. J. Am. Soc. Mass Spectrom. 2000, 11, 659–663.

7. Ishihama, Y.; Katayama, H.; Asakawa, N.; Oda, Y. Highly robust stainless steel tips as microelectrospray emitters. Rapid Commun. Mass Spectrom. 2002, 16, 913–918.

8. Cloupeau, M.; Prunet-Foch, B. Electrostatic spraying of liquids in cone-jet mode. J. Electrostat. 1989, 22, 135–159.

9. Chowdhury, S. K.; Katta, V.; Chait, B. T. Probing conformational changes in proteins by mass spectrometry. J. Am. Chem. Soc. 1990, 112, 9012–9013.

10. Sze, S. K.; Ge, Y.; Oh, H.; McLafferty, F. W. Top down characterization of larger proteins (45 kDa) by electron capture dissociation mass spectrometry. Proc. Natl. Acad. Sci. USA. 2002, 99, 1774–1779.

11. Bigwarfe, P. M.-Jr.; White, T. P.; Wood, T. D. Polyaniline-coated nanoelectrospray emitters: performance characteristics in the negative ion mode. Rapid Commun. Mass Spectrom. 2002, 16, 2266–2272.

12. Ito, M.; Tchoua, U.; Okamoto, M.; Tojo, H. Purification and properties of a phospholipase A2/lipase preferring phosphatidic acid, bis(monoacylglycerol) phosphate, and monoacylglycerol from rat testis. J. Biol. Chem. 2002, 277, 43674–43681.

13. Tojo, H.; Japan Patent 2003-028849, July, 2001

14. Hook, G. E. Alveolar proteinosis and phospholipidoses of the lungs. Toxicol. Pathol. 1991, 19, 482–513.

15. Seeger, W.; Pison, U.; Buchhorn, R.; Obertacke, U.; Joka, T. Surfactant abnormalities and adult respiratory failure. Lung 1990, 168, 891–902 (Suppl).

16. Hohlfeld, J. M.; Tiryaki, E.; Hamm, H., Hoymann, H. G., Krug, N.; Haverich, A.; Fabel, H. Pulmonary surfactant activity is impaired in lung transplant recipients. Am. J. Respir. Crit. Care Med. 1998, 158, 706–712.

17. Zirrolli, J. A., Davoli, E., Bettazzoli, L., Gross, M., and Murphy, R. C. Fast atom bombardment and collision-induced dissociation of prostaglandins and thromboxanes: some examples of charge remote fragmentation. J. Am. Soc. Mass Spectrom. 1990, 1, 325–335.

18. Hankin, J. A., Wheelan, P., and Murphy, R. C. Identification of novel metabolites of prostaglandin E2 formed by isolated rat hepatocytes. Arch. Biochem. Biophys. 1997, 340, 317–330.

19. Takagi, S., Tojo, H., Tomita, S., Sano, S., Itami, S., Hara, M., Inoue, S., Horie, K., Kondoh, G., Hosokawa, K., Gonzalez, F. J., Takeda, J. Alteration of the 4-sphingenine scaffolds of ceramides in keratinocyte-specific Arnt-deficient mice affects skin barrier function. J. Clin. Invest. 2003, 112, 1372–1382.

BRIEF DESCRIPTION OF THE DRAWINGS

FIGS. 1D, 1E and 1F show photographs of fused silica capillary emitters with the tapered tip coated with PFPO. (1D: treated with HF. 5 cm in length, and 20-µm inner and 150-µm outer diameters, and the inset shows a magnified view of its tip; 1E: HF-treated. 5 cm in length, and 20-µm inner and 360-µm outer diameters; 1F: a pulled capillary of 5.2 cm in length, and 50-µm inner and 360-µm outer diameters.) The inner diameter of the outlet orifice 3 is 15 µm (New Objective, MT). Its internal coating was limited around the tip, although full internal coating of 15-µm ID capillaries with no internal taper was possible.

FIG. 4 shows MS analyses of tryptic peptides of reduced and alkylated bovine serum albumin (0.1 pmol). An etched, PFPO-coated emitter of 20 μm ID/150 μm OD was used. (4A: A TIC chromatogram in the positive ion mode. Experimental conditions are described in the text.; 4B: A full-scan MS spectrum of peptides included in a peak eluted at the retention time of 11.3 min indicated by an asterisk.; 4C: A full-scan MS/MS spectra of $[M+2H]^{2+}$ ions of m/z 653.5. A nominal collision energy was 35%.; and 4D and E: A comparison of base peak chromatograms obtained with internally POPF-coated and uncoated capillaries that connect an injector and a column inlet, respectively.)

FIG. 8 shows analysis of prostaglandins by capillary HPLC/ion-trap MS in the negative-ion modes using aqueous acetonitrile. An etched, PFPO-coated emitter of 20-μm ID and 150-μm OD and an ESI voltage of 1.7 kV were used. The HPLC system used was the same as in FIG. 4. The capillary that connect an injector and a column inlet are internally coated with POPF. An 1-μl aliquot of mixtures of $PGD_2$, $PGJ_2$, and 15-deoxy-$\Delta^{12, 14}$-$PGJ_2$ (0.5 pmol each) was gently drawn into a microsyringe containing 10-μl solvent A, and then injected onto a trap column (0.3×5 mm) fitted to a 10-port Valco valve. The column was pre-equilibrated with 15% solvent B and developed with a linear concentration gradient of solvent B from 15 to 30 in 1 min and from 30 to 45% in 20 min at the flow rate of ~1.5 μl/min. 8A: base peak chromatogram (m/z 200–450); Full scan MS spectra for 8B: $PGD_2$; 8C: $PGJ_2$; and 8D: 15-deoxy-$\Delta_{12}, ^{14}$-$PGJ_2$.

DESCRIPTION OF THE PREFERRED EMBODIMENT

The present invention will be described in more detail with reference to the preferred embodiments thereof. However, the following embodiments are representative of the present invention, and are not intended to limit the scope thereof.

(Electrospray Emitters)

Figures 1A, 1B, 1C:
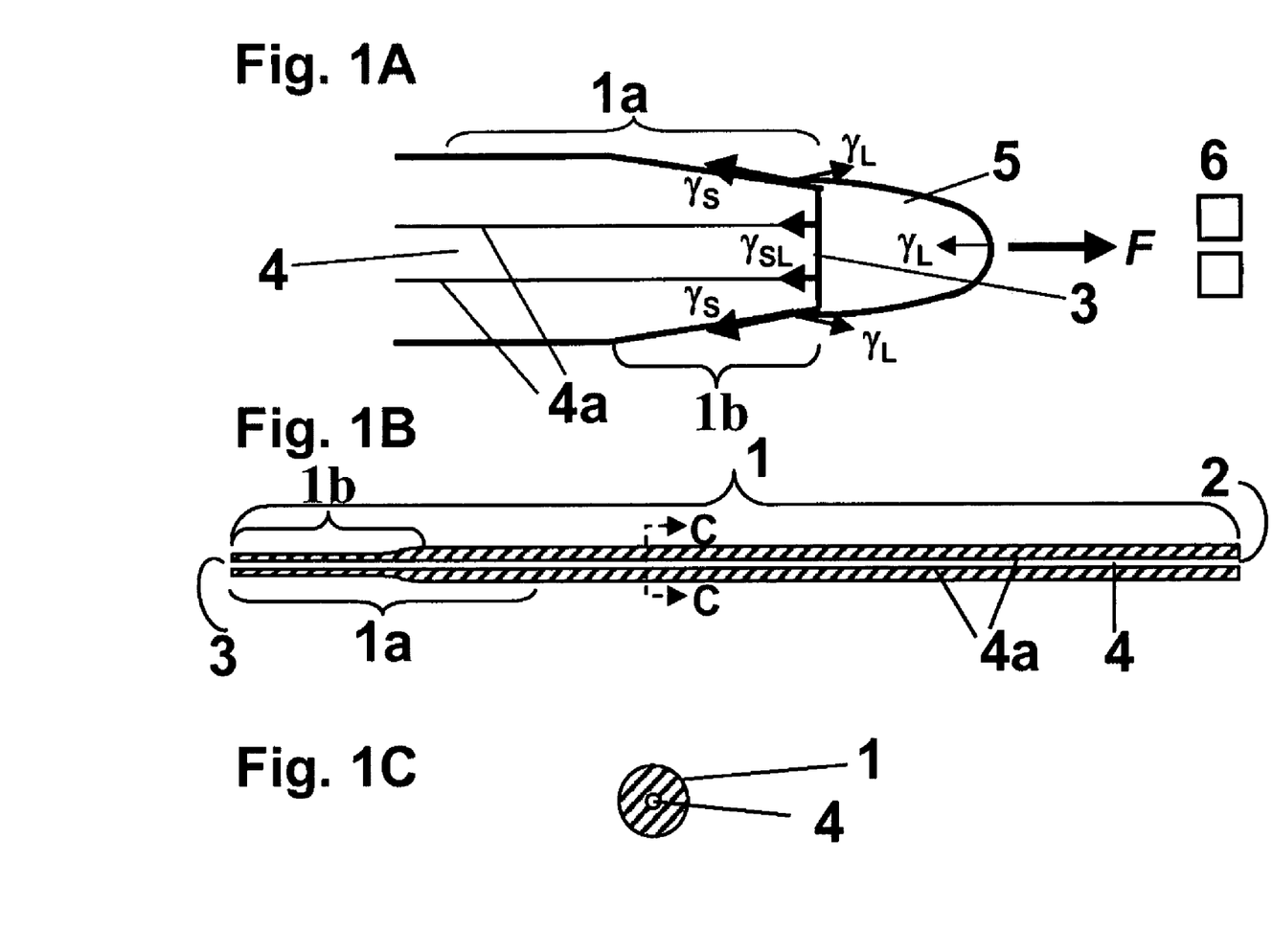
FIG. 1A shows the effect of the surface tension of emitter body on the size of a droplet formed at the emitter outlet.
FIG. 1B shows the cross-sectional view in the longitudinal direction of the electrospray emitter of one of the embodiments of the present invention.
FIG. 1C shows the cross-sectional view of the electrospray emitter at Line C-C of FIG. 1B (1: the emitter body (capillary); 1a: a polyimide-peeled portion of the exit end that are coated with PFPO; 1b: the tapered region of the exit end; 2: the inlet orifice; 3: the outlet orifice; 4: the channel connecting 2 and 3; 4a: the wall of 4; 5: a pre-Taylor cone drip at the emitter exit tip; 6: the counter electrode; F: electric force applied) In FIG. 1A, the symbol g denotes the surface tension, and the subscripts S, L, and SL the fused silica/air, water/air, and fused silica/water interfaces, respectively.

FIG. 1B shows one of preferred embodiments of the electrospray emitter of the present invention. As shown in FIG. 1B, the electrospray emitter comprisies a emitter body 1 comprising an inlet orifice 2, an outlet orifice 3 and a channel 4 connecting the inlet orifice 2 and the outlet orifice 3. In the present invention coating of the outer surface of the exit end with a material of low surface energy is essential for efficient electrospraying. Accordingly, in the emitter as shown in FIG. 1B, the coating is formed on the outer surface 1a of the exit tip, preferably on the outer surface 1b.

Figure 1D:
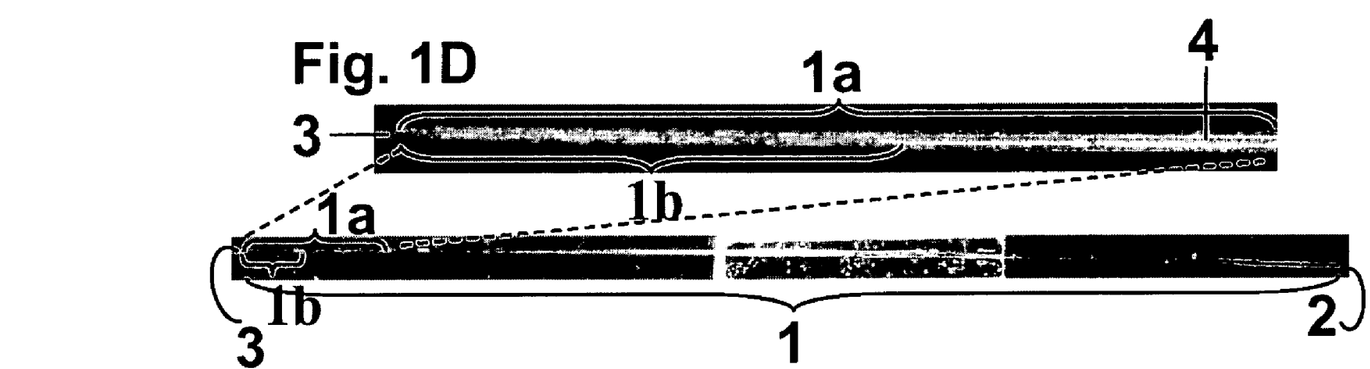
Figure 1E:
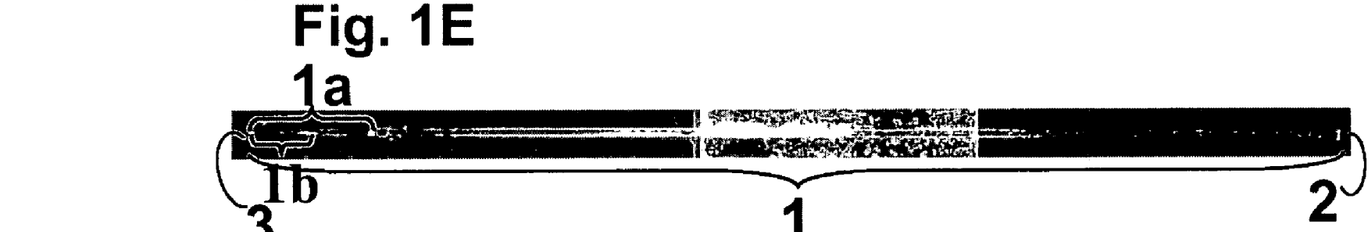
Figure 1F:
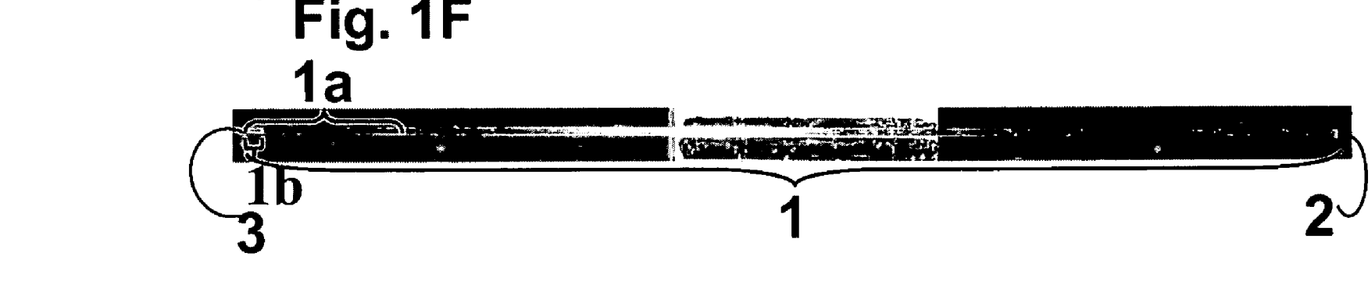

In the present invention, in addition to the outer surface of the exit tip, the remaining surface of the emitter body may be coated with a material with low surface energy. In addition to the coating at the exit tip, the inner surface 4a of the channel 4 may be coated with a material of low surface energy at least partly at the outlet end. In a preferred embodiment, the coating can be formed on the entire inner surface 4a of the channel 4. For example, in the emitters as shown in FIGS. 1D and 1E, the PFPO coating is formed on the entire inner surface 4a of the channel 4 in addition to the coating formed on the outer surface 1b. In the emitter as shown in FIG. 1F, the PFPO coating is formed on the outer surface 1b and on limited areas of the inner surface at the exit end. However, in these figures, the PFPO coating cannot be seen because of its colorlessness and transparency.

As used herein, the term "low surface energy" means, for example, an energy content of a solid surface (equivalent to the surface tension of a liquid) of not more than 20 mN/m, preferably 5 to 20 mN/m, more preferably 6 to 12 mN/m. The materials with low surface energy, which can be used in the present invention, are not specifically limited as far as they have suitable low surface energy, and can be coated on the emitter body without impairing the performance of the electrospray emitter. Suitable materials with low surface energy include, for example, a fluoropolymer and fluorinated compound. Suitable fluoropolymer and fluorinated compound may be selected from perfluoropolyoxetane, perfluorourethane, fluoropolymer elastomers, polytetrafluoroethylene, fluoroalkyl monosilane, polymeric perfluoroether di- and poly-silane, and perfluorooctal and perfluoropolyether with an epoxy, hydroxy, acrylate or isocyanate functional group. Most preferred is perfluoropolyoxetane (PFPO). PFPO usually has a critical surface tension of 12 mN/m at room temperature.

The emitter bodies can be made of fused-silica capillary, but of any material suitable for electrospray emitters including, without limitation, glasses, glass ceramics, aluminosilicate glasses, polypropyrene, and stainless steel. The PFPO coating enabled the capillary of blunt end in the absence of polyimide coating to spray water.

Tapered capillary tip is preferred to ensure stable spraying and increased detection sensitivity on MS (refer to, for example, D. Gale, et al., Rapid Commun. Mass Spectrom. 1993, 7, 1017–1021; M. Emmett, et al., J. Am. Soc. Mass Spectrom. 1994, 5, 605–613; G. Valaskovic, et al., Anal. Chem. 1995, 67, 3802–3805; and M. Wilm, et al, Anal. Chem. 1996, 68, 1–8). Accordingly, as shown in FIG. 1B, the emitter body 1 is tapered externally toward the outlet orifice 3. For ESI operation at the flow rate of greater than about 0.1 μl/min, which are used for conventional capillary HPLC., this configuration of the emitter body 1 is practical to avoid clogging at the emitter exit. For ESI operation, such as nanospraying, at further lower flow rate, the outer and inner walls of the emitter body 1 are more preferably tapered toward the outlet orifice 3. In this case, the emitters with a blunt end should be able to spray water with efficiency lower than those with a tapered end.

Pulling capillaries, using a commercially available pulling device, can produce their tapered ends (M. Wilm, et al., Anal. Chem. 1996, 68, 1–8). These pulled capillaries can also be purchased from commercial sources, such as New Objective (Cambridge, Mont.). Pulling capillary let both inner and outer diameters narrower. Alternatively, the tapered tip of emitters can be produced by hydrofluoric acid (HF) treatment (D. Gale, et al., Rapid Commun. Mass Spectrom. 1993, 7, 1017–1021). Polyimide coating (if any) was burned off by an appropriate length, e.g., 7 mm, from one end of a capillary of desired length, typically 3–5 cm, and then dipped into a HF solution (46% in the following examples) with gentle stirring for suitable times, depending on the outer and inner diameters of capillaries, e.g., for 20 min for a capillary of 20 μm inner (ID) and 150 μm outer (OD) diameters. During the treatment a droplet of HF solution grew larger near a junction between polyimide coating and fused silica surface; the droplet was occasionally blew off by nitrogen flow. In contrast to pulling methods, HF treatment can keep the inner diameter of capillaries at the tip intact, which is important to reduce the risk of particle clogging, especially on high-throughput work. To ensure this during HF treatment, a fluid, preferably water, was pumped through a capillary at a flow rate suitable for its inner diameter, for example, at 200 nl/min for capillaries of 20 μm diameters. A gas, such as air or a non-reactive gas, preferably nitrogen, is also usable for this purpose. Then the lumen of capillary was flushed and dried by nitrogen gas flow and further dried at 40° C.

The size of the emitter body (such as length, inner diameter and outer diameter) is not specifically limited, and can be designed by a skilled person in the art depending on the application thereof. However, typical emitter body may have a length of 30 to 50 mm. The outer diameter and the inner diameter of the outlet orifice of the emitter are not specifically limited. However, the outer diameter and the inner diameter may range from 150 to 375 and from 10 to 50, respectively. In addition, suitable emitter bodies can be purchased from various commercial suppliers, such as New Objective (Cambridge, Mass.).

(Method of Making Electrospray Emitter)

As mentioned above, another aspect of the present invention provides a method for making an electrospray emitter. Such a method comprises: providing an electrospray emitter comprising an emitter body having an inlet orifice, an outlet orifice and a channel connecting the inlet orifice and the outlet orifice; and forming a coating with a material of low surface energy at least on the outer surface of the exit end of the emitter body. In one embodiment, application of the coating can be carried out, for example, by dipping the portion of the emitter body into a solution of the material with low surface energy in a suitable solvent. After dipping, the solvent is allowed to evaporate, and then leaving the coating on the portion of the emitter body dipped in to the solution.

More specifically, the electrospray emitter of the present invention can be prepared in the following manner. For PFPO coating of capillaries (emitter body) etched by the method described above or of pulled capillaries purchased from New Objectives, the polyimide-peeled tips or non-coated tips were immersed in an appropriate concentration (e.g., from 0.1 to 0.001 wt. % of PFPO) of PFPO in perfluorohexane for from about 1 min. to 10 minutes. Capillaries of any dimensions can be coated, but for capillary HPLC the ones of 10–50 μm in inner diameter (ID) are preferable to avoid clogging during HPLC operation. In etched capillaries of 5 cm in length with intact lumen of 10–50 μm in diameter, simply immersing them in PFPO solutions can coat both the entire length of capillary lumen and outer silica surface, while coating of luminal surface of pulled capillaries with a smaller-bore exit was only limited in their tips. PFPO solutions will be pumped through the capillaries, if necessary, to coat their whole inner surface. After dipping the tips at higher concentrations of PFPO, such as 0.1%, flushing the lumen by air or a non-reactive gas, such as nitrogen was preferable to avoid clogging at the tip orifice, but not always needed. PFPO-treated capillaries stand for at 60° C. for 60 min, and then usable for ESI/MS experiments. The thickness of the coating is about 10 nm for coating with 0.1% PFPO. Some examples of the emitter of the present invention are shown in FIGS. 1B–F. The PFPO coatings are colorless and transparent, which makes the solvent flow in the emitter tip visible.

Figure 2:
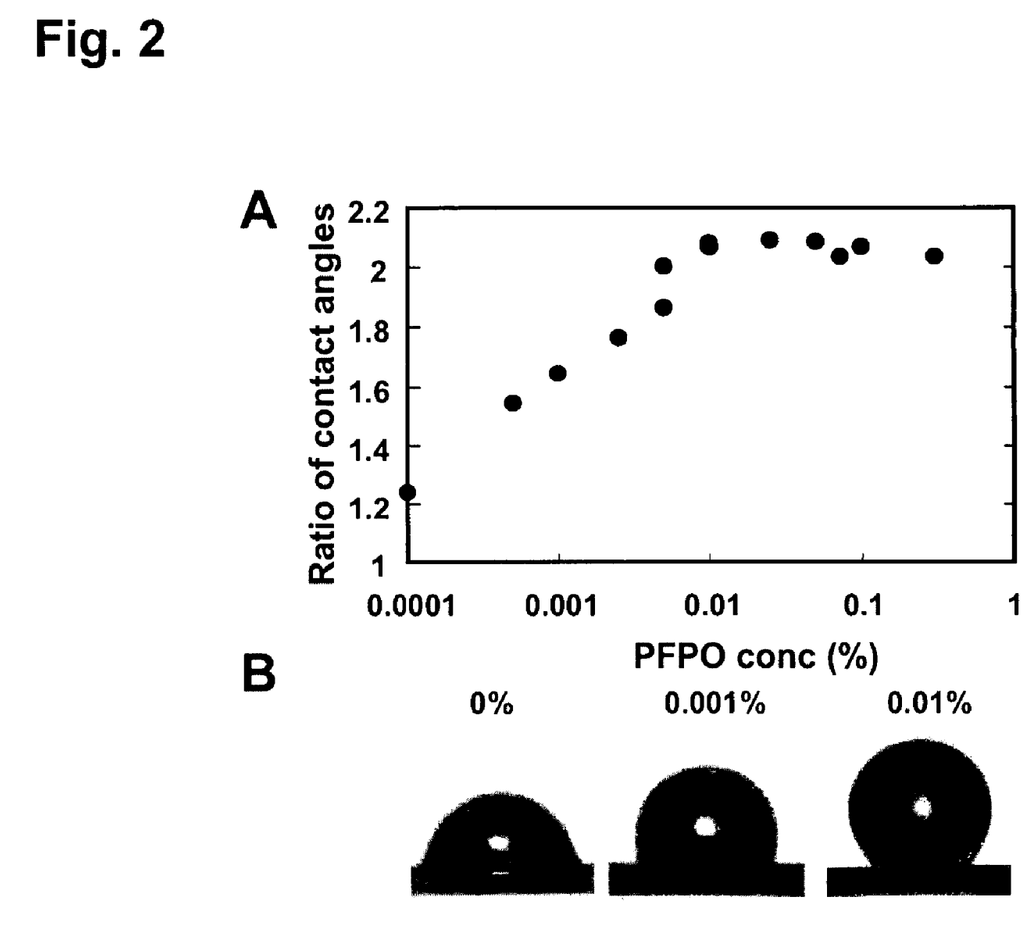
FIG. 2A shows contact angles of the surface of the emitter tips coated with the indicated concentrations of PFPO. The ordinate indicates the ratio of the contact angles of a PFPO-coated to an uncoated tip.
FIG. 2B shows photographs of water droplets on capillary tips coated with 0.001% and 0.01% PFPO, compared with those on a non-coated tip.

FIGS. 2A and 2B show the dependence of the contact angles of water on emitter tip surface on PFPO concentrations. The ratio of the contact angles of a PFPO-coated to an uncoated tip increased with an increase in PFPO concentration, leveled off around 0.01%, and reached a maximal value of about 2.08 (corresponding to the contact angle of about 122°). PFPO concentrations were preferably less than 0.1% to avoid clogging with the coating material during a drying process, and the optimal concentrations for effective spraying depended on the inner and outer orifice diameters.

(Tubular Connectors For Connecting Emitters with Analytical Devices)

The present invention also provides a tubular connector (capillary, tubing, connecting line) for connecting an electrospray emitter and an analytical device, which can prevent sample losses. Such tubular connector comprises a tubular connector body comprising an inlet orifice, an outlet orifice and a passage communicating between the inlet orifice and the outlet orifice; and a coating formed on at least a portion of the inner surface of the connector body with a material with low surface energy. Preferably, the inner surface of the connector body is entirely coated with a material with low surface energy. Suitable materials of low surface energy include, for example, a fluoropolymer and a fluorinated compound. Preferred fluoropolymers and fluorinated compounds are as already described. Most preferred is perfluoropolyoxetane. The tubular connector body may be made of any conventional materials such as fused-silica.

The coating can be formed on the inner surface of the connector body by the method as described above, e.g., a method comprising pumping an appropriate solution containing a material with low surface energy through a channel in the connector body. The person skilled in the art can choose the size of the connector (e.g., length, inner and outer diameter) in accordance with the technical knowledge in this field. Use of the connector as described can prevent loss of analytes during delivery between the emitter and analytical devices, e.g., liquid chromatography.

Hereinafter the present invention is described in more detail with reference to EXAMPLES, but is not deemed to limit the scope of the present invention thereto.

EXAMPLE 1

Preparation of Capillaries with the Internal Surface Coated with PFPO

Fused-silica capillaries with a polyimide coating are now a standard tubing system for capillary HPLC, and it is well known that their inner surface has a capacity for binding charged and/or hydrophobic analytes, leading to a significant loss during their delivery in an HPLC tubing system. To prevent those sample losses, the internal surface of fused-silica capillaries was coated with PFPO. An appropriate concentration of PFPO (0.1–0.001%, more preferably 0.005–0.02%) was pumped through a capillary. It was flushed by a nitrogen flow, and incubated for 60 min at 60° C. and then overnight at 40° C.

EXAMPLE 2

Performance of the Emitter Tips with Water-rich Solvent

At the initial stage of gradient elution on reverse-phase HPLC being frequently used for high-throughput proteomics and metabolomics, emitters must electrospray water-rich solution, e.g., 2% acetonitrile and 0.1% formate in water, in the stable cone-jet mode (Cloupeau, M.; Prunet-Foch, B., J. Electrostat. 1989, 22, 135–159.) immediately after a high voltage is applied. To test whether the emitters of this invention meet this requirement, their efficiency of spraying distilled water was examined using an etched, PFPO-coated emitter with no internal taper at the tip by visual inspection and stability of total ion current (TIC) with an ion-trap mass spectrometer LCQ (ThermoFinnigan, Calif.). In this and subsequent examples, LCQ was used for testing performance of the emitters because of its good connectivity for HPLC, but they can be used with any type of mass spectrometers; fine-tuning of the experimental parameters including dimensions and types of emitter, and MS settings will be required to obtain an optimal overall performance of an HPLC/MS system, depending on types of mass spectrometer used. Distilled water was delivered to an etched, PFPO-coated emitter of 20 μm ID/150 μm OD with a syringe pump at the flow rate of 0.8 μl/min being suitable for HPLC on a capillary column of 0.1–0.2 mm in ID. The counter electrode voltage of 1.8 kV was applied and total ion current (TIC) of m/z 150–2000 was recorded for 20 min with LCQ; optimal voltages depended on dimensions of the emitters and the surface tension values of sample solutions, typically in the range of 1.2–2.0 kV. The emitter tip was placed at an appropriate distance, typically about 3 mm, in front of a heated capillary inlet of LCQ with a xyz stage (AMR, Tokyo). Using these setups PFPO-coated emitters can stably spray distilled water as shown in FIG. 3A.

Figure 3:
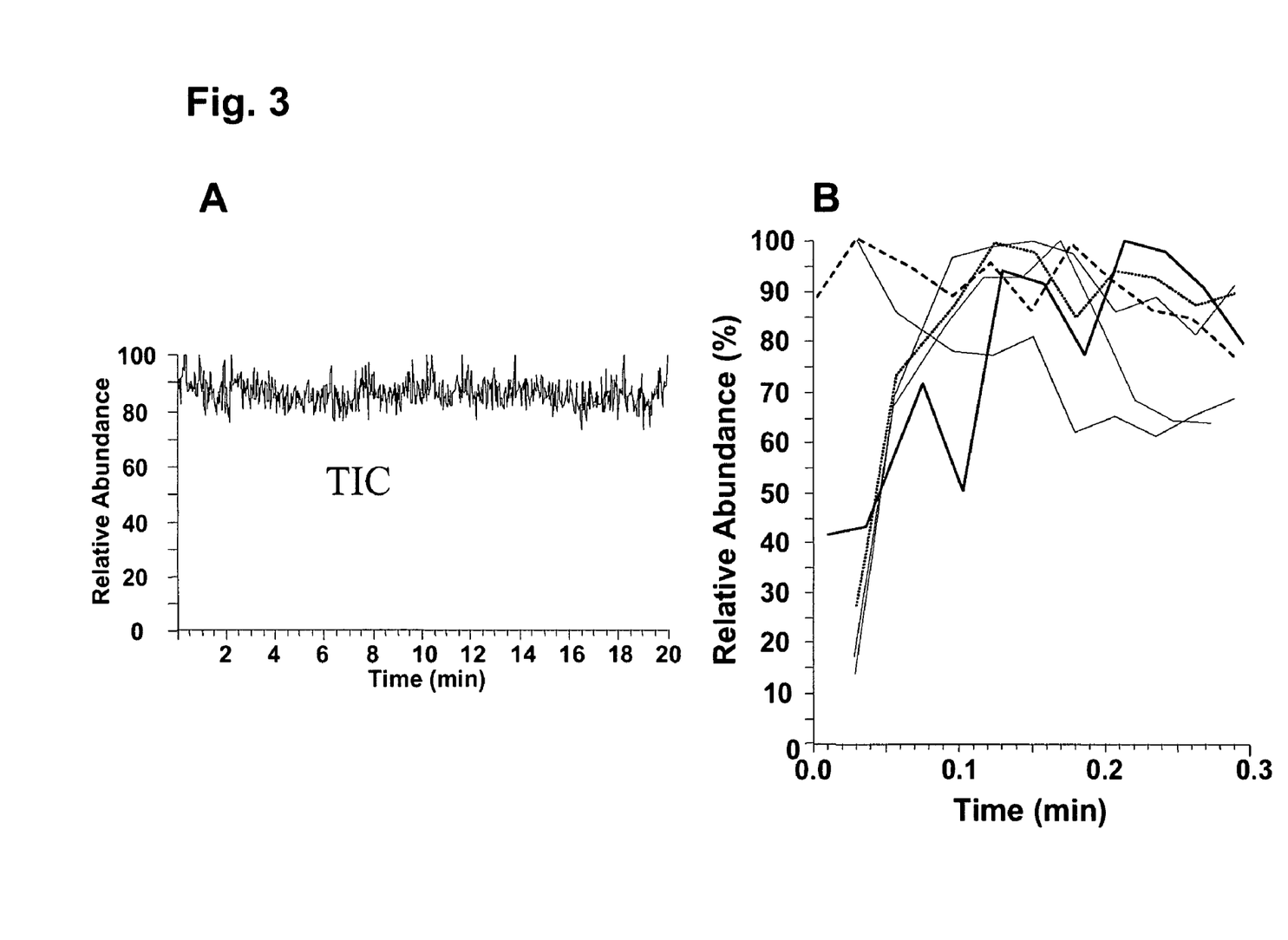
FIG. 3 shows performance of PFPO-coated emitters with distilled water (3A: Stability of spraying distilled water from a PFPO-coated emitter; and 3B: Rapid onset of electrospray from distilled water, a high surface tension solvent). The total ion current traces (m/z=150–2000) from 6 experiments using the indicated time lags between starting a pump and a high voltage applied to the emitter are superimposed.

It is desirable to keep the high voltage off on washing column between runs, and on injecting sample, otherwise contaminants do enter a mass spectrometer. With the voltage off, droplets in various sizes grows at the tip of emitter, which often prevents conventional, uncoated or metal-coated pulled emitters from spraying after the high voltage is applied again on the next run. To mimic those unfavorable conditions encountered on HPLC/MS, we first started delivering distilled water to a PFPO-coated emitter through a syringe pump and then applied a high voltage after some lag times during which water droplets varying in size form at the emitter tip. All TIC traces of m/z 150–2000 in the positive ion mode from experiments using 6 different lag times (0, 0.5, 1, 1.5, 2, and 2.5 min from the onset of charging) shows rapid onset of stable electrospray from distilled water in the cone-jet mode within about 0.15 min (FIG. 3C). These results demonstrate that PFPO-coated emitters are compatible with high-throughput HPLC/MS analyses using an autosampler injection and water-rich solvent for column initialization as well as direct infusion analyses of samples in aqueous solution.

Figure 4:
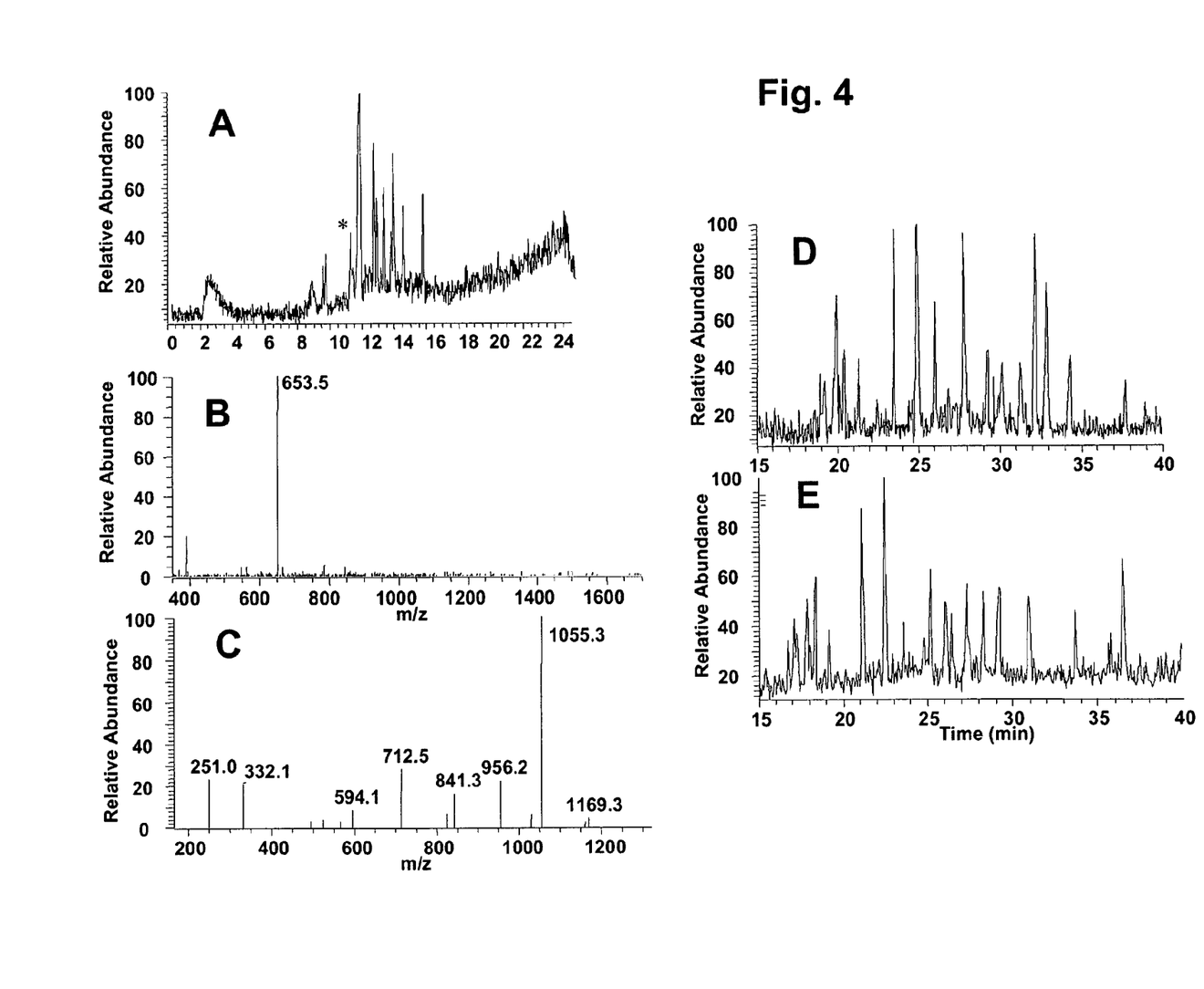
Figure 5:
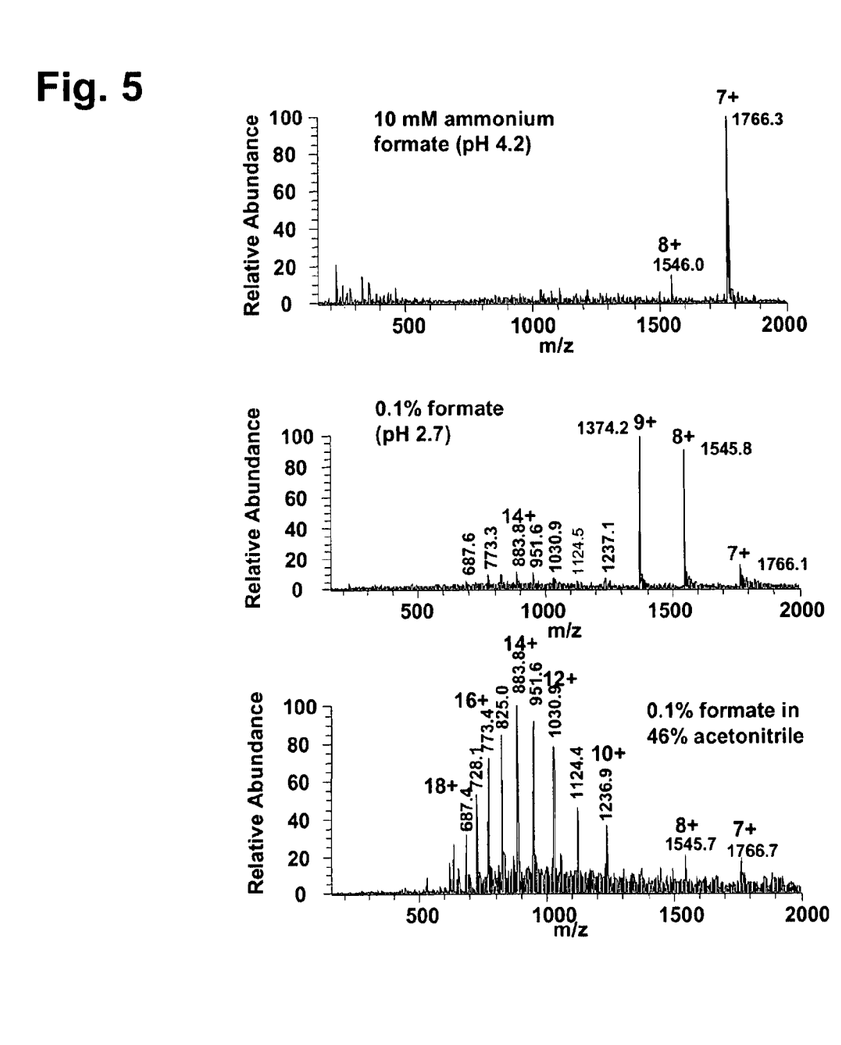
FIG. 5 shows positive ion mass spectra of cytochrome c (1 μM) in distilled water containing the indicated additives. The spectra were accumulated for 20 scans. An etched, PFPO-coated emitter of 20 μm ID/150 μm OD was used.

FIG. 4A shows a TIC chromatogram of tryptic peptides of 0.1 pmol reduced and alkylated bovine serum albumin on a Magic C18 column (0.2×50 mm, Michrom BioResources, Inc.) in the positive ion mode. The column was pre-equilibrated with solvent A (2% acetonitrile and 0.1% formate in water), and developed with a linear concentration gradient of solvent B (90% acetonitrile and 0.1% formate): from 2 to 60% in 20 min at the flow rate of about 1 μl/min. The total flow rate of Magic2002 pumps (Michrom BioResources, Inc.) was set at 50 μl/min, and the flow rate across the capillary column was regulated with a Magic variable splitter (Michrom BioResources, Inc.). A 20 μm ID and 150 μm OD PFPO-coated emitter was directly connected to an outlet stainless fitting of the column to minimize a peak broadening by diffusion. Input of a contact signal from HPLC to LCQ started applying an ESI voltage (e.g., 1.7 kV) to the column outlet fitting. Stable electrospray immediately occurred from water-rich solvent A, and last until the end of gradient (FIG. 4A). A full-scan spectrum containing ions of m/z 653 eluting as a base peak (indicated by an asterisk in FIG. 4A) at the retention time of 11.3 min, and its MS/MS spectrum are shown in FIGS. 4B and C, respectively. No signal derived from PFPO was observed in the ESI mass spectra over the entire gradient range. The detection sensitivity with the emitters of the present invention was generally similar to that with a metal-coated pulled capillary, but tended to be enhanced for hydrophobic peptides eluting later compared to the latter. PFPO-coated emitters are so robust to be usable for more than 500 hours on reverse phase HPLC/MS of tryptic peptides of proteins separated from crude sources, such as two-dimensional electrophoresis and HPLC.

A base peak chromatogram of tryptic peptides of 0.1 pmol reduced and alkylated bovine serum albumin on a Magic C18 column (0.2×50 mm) in FIG. 4D was obtained using a capillary with the internal PFPO coating that connected an autoinjector and a column. Compared with the use of a connecting capillary with no internal coating (FIG. 4E), the use of the former gave good recovery of hydrophobic peptides eluting later.

We next applied the emitters of the present invention to examine the effects of organic solvent concentrations on ESI mass spectra of proteins. The envelopes of peaks of multiply charged positive ions of horse heart cytochrome c (1 μM) shifted towards lower m/z values with their maximal intensities at 1766.3, 1374.2, and 883.8 mass units (corresponding to the charges +7, +9, and +14, respectively) with an increase in denaturing power of solvents used: water containing 10 mM ammonium formate (pH 4.2)<water containing 0.1% formic acid (pH 2.73)<46% acetonitrile containing 0.1% formic acid, respectively. This is consistent with the results of previous studies, and those shifts to lower m/z was attributed to the degrees of exposure of ionizable side chains to solvent by protein conformational changes (S. Chowdhury, et al., J. Am. Chem. Soc. 1990, 112, 9012–9013.). The emitters of this invention will therefore help study conformations and unfolding/folding of proteins in gas-phase as a function of their conformation in solution including native conformation in purely aqueous solutions. Moreover, the recent development of ultra-high resolution Fourier transform ion cyclotron resonance MS are drawing much attention to analyses of whole proteins by MS including MS/MS without protease digestion (S. Sze, et al., Proc. Natl. Acad. Sci. USA. 2002, 99, 1774–1779.). Organic solvents are usually included in sample solutions to assist ESI by conventional emitters, but are prone to cause uncontrollable denaturation and aggregation of proteins. The present emitters compatible with MS analyses in their absence will be helpful in studying whole proteins.

EXAMPLE 3

Capability of the Emitter for Negative Ion MS

There is an increased risk of corona discharge or arcing in the negative ion mode versus in the positive ion mode (Ceck, N. B.; Enke, C. G., Mass Spectrom. Rev. 2001, 20, 362–387). In particular, conventional metal-coated emitters are prone to experience corona discharge that damages a coated tip. This prevents a stable spraying of negative ions, thereby hindering their coupling to HPLC or other separation methods that require a stable operation of ESI for a longer time period. Very recently, nanoelectrospray emitters coated with polyaniline, a conductive polymer, was reportedly resistant to electrical discharge and durable for at least an hour in the negative ion mode (P. Bigwarfe, et al., Rapid Commun. Mass Spectrom. 2002, 16, 2266–2272). The tips of PFPO-coated emitters are electrically non-conductive. This virtually eliminates electrical discharge and allows stable electrospray in the negative ion mode as well as in the positive ion mode. This is exemplified by mass spectra of peptides, ceramides, phospholipids, and prostaglandins (PG) as follows.

Angiotensin II (0.1 μM) dissolved in 7 volumes of solvent A and 3 volumes of solvent B was continuously infused through a 20 μm ID and 150 μm OD PFPO-coated emitter at the flow rate of 0.4 μl/min, and the onset of electrospray was initiated with an applied voltage of 1.8 kV. LCQ was separately tuned and spectra were individually acquired for the positive and negative ion scans. Angiotensin II contains an acidic and 2 basic residues with a calculated pI of 7.81, and thus is positively charged in the presence of 0.1% formate (pH 2.73), unfavorable for the formation of negative ions in solution. The negative ion spectrum, however, exclusively contained abundant, singly charged $[M-H]^-$ ions at m/z 1044.6, compared to the positive ion spectrum with $[M+2H]^{2+}$ ions of m/z 524 predominant (FIGS. 6A and B). The signal intensity of a base peak in the positive ion spectrum were 8.4 times that in the negative ion spectrum, but their signal-to-noise (S/N) ratios were similar to each other, consistent with lower levels of chemical noises and contaminant peaks in the negative ion mode. These results indicate a potential importance of applying negative ion MS measurements with PFPO-coated emitters to proteomics studies.

Another example using less polar solvent mixtures is a comparison of positive and negative spectra for three ceramide species that were acquired simultaneously by an alternate polarity switching (M. Ito, et al., J. Biol. Chem. 2002, 277, 43674–43681; and Tojo, H.; Japan Patent Publication 2003-028849). N-Lignoceroyl-4-sphingenine (S), N-lignoceroyl-sphinganine (Sa), and N-stearoyl-4-hydroxy-sphinganine (P), 0.1 μM each, were dissolved in hexane/2-propanol/ethanol; 5:4:1 (v/v/v) containing 5 mM ammonium formate. The mixtures were sprayed through a 50 μm ID and 150 μm OD PFPO-coated emitter at the flow rate of about 2 μ/min with an applied voltage of 1.4 kV. The low surface tension of the solvent system used and the emitter tips led to stable electrospray in the positive and negative ion modes with the alternate polarity switching controlled by LCQ's Xcalibur software. The signal intensity of a base peak in the positive ion spectrum were about 20 times that in the negative ion spectrum, but the S/N ratio was somewhat better in the latter. $[M+H]^+$ ions of Sa, S, and P at m/z 652.5, 650.3, and 584.4, respectively, and the corresponding $[M-H]^-$ ions with m/z values smaller by 2 mass units were predominantly observed (FIGS. 6C and D). A peak of positive ions of m/z 584.4 arose from loss of $H_2O$ from S, characteristic of 4-sphingenine containing ceramides. The solvent system used contained 5 mM formate to enhance ionization efficiency of ceramides, which was prone to form formate adduct ions in the negative ion mode. Applying an in-source low voltage (ca. 20V) prevented forming these adducts, and helped generate structurally informative $[M-H]^-$ ions of ceramides (FIG. 6D).

Figure 6:
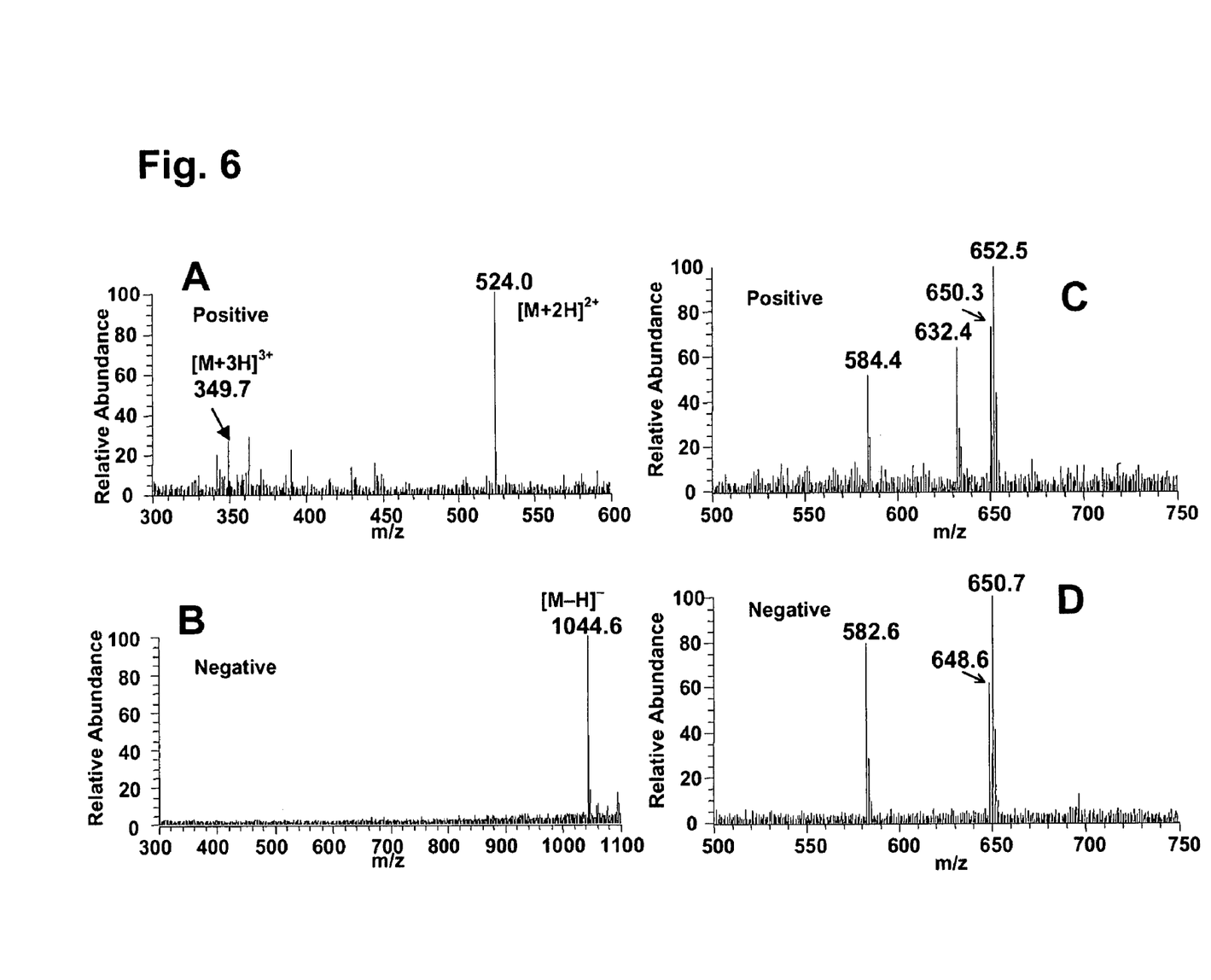
FIG. 6 shows positive and negative ion mass spectra of angiotensin II and ceramides (0.1 μM each). Angiotensin II (6A and B) and ceramide mixtures containing N-Lignoceroyl-4-sphingenine, N-lignoceroyl-sphinganine, and N-stearoyl-4-hydroxy-sphinganine (6C and D). Experimental setups are described in the text. Ceramide spectra were acquired in the alternate positive and negative ion mode.
Figure 7:
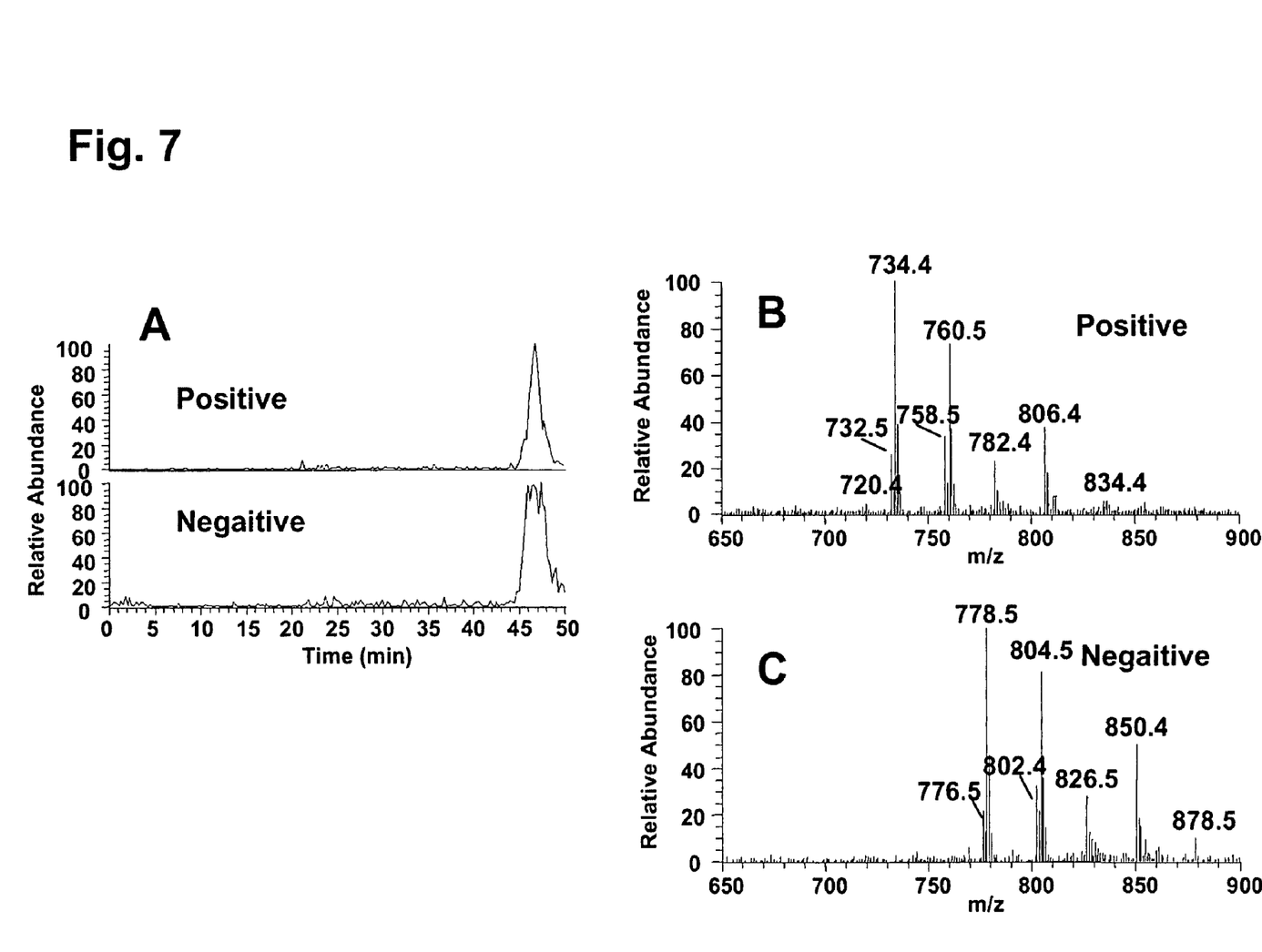
FIG. 7 shows HPLC/ESI MS of phosphatidylcholine in murine lung lavage in the alternate positive and negative ion mode. (7A: mass chromatograms of $[M+H]^+$ and $[M+HCOO]^-$ ions of DPPC at m/z 734.4 and 778.5, respectively; and 7B and C: positive and negative ion mass spectra of lung lavage phosphatidylcholines eluted around the retention time of 46.8 min. Negative ions were ionized as formate adducts with 46-mass unit larger than the corresponding $[M-H]^-$ ions.).

Mass spectrometry in proteomics handles peptides of more or less similar chemical properties, but metabolomics needs high throughput identification of huge numbers of metabolites with the vast spectrum of hydrophobicities and proton affinities, which in turn ideally need ESI conditions customized to each analyte during chromatography. As the first step for this challenging task, monitoring both positive and negative ions on a single chromatographic run would help in identifying the structures of analytes. This example shows analysis of the major lung surfactant, dipalmitoyl-sn-glycero-3-phosphocholine (DPPC), in murine lung lavage by normal-phase HPLC/ESI-MS in the alternate polarity switching mode. DPPC levels increase in pulmonary alveolar proteinosis (G. Hook, et al., Toxicol. Pathol. 1991, 19, 482–513), but decrease in severe lung diseases including adult respiratory distress syndrome in severe shock (W. Seeger, et al., Lung 1990, 168, 891–902 (Suppl)) and probably rejection after lung transplantation (J. Hohlfeld, et al., Am. J. Respir. Crit. Care Med. 1998, 158, 706–712). Hence, its analysis would be clinically important, such as in critical care management. Normal-phase HPLC on a Lichro-Sphere Si-100 (1×150 mm) was connected to the same emitter as previously used for ceramide analysis (FIG. 6). An aliquot of lipids extracted from right lung lavage by the method reported previously (M. Ito, et al., J. Biol. Chem. 2002, 277, 43674–43681) was injected to the column pre-equilibrated with solvent C, hexane/2-propanol/ethanol (4:5:1 v/v), at the flow rate of 50 μl/min, and the column was developed with a linear gradient of solvent D, solvent C/1 M ammonium formate in water/water (100: 2.24: 9.76 v/v/v) from 0 to 100% in 20 min and then holding at 100% for 30 min at the flow rate of 50 μl/min. The effluent was split with a tee to yield a flow rate across the column of about 1.5 μl/min, and monitored with a LCQ in either data dependent negative or positive ion MS/MS mode as well as in alternate positive and negative ion full scan mode on a single run. Since DPPC contains a quaternary ammonium ion, ESI generates its abundant $[M+H]^+$ ions, but hardly $[M-H]^-$ ions; the presence of formate ions in elution solvents promoted forming formate adduct ions of phosphatidylcholine (FIGS. 7B and C). Mass chromatograms of the $[M+H]^+$ or $[M+HCOO]^-$ ions of DPPC show a single peak at the retention time of 46. 8 min (FIG. 7A). The signal intensity of $[M+H]^+$ ions of DPPC (m/z 734) were 24 times that of the corresponding $[M+HCOO]^-$ ions, but the S/N ratios were comparable. Murine lung lavage mainly contained di-saturated DPPC, but did appreciable amounts of species with an unsaturated acyl group: C16:0/C18:1 (m/z 760), C16:0/C18:2 (m/z 758), C16:0/C22:6 (m/z 806), C16:0:C16:1 (m/z 732), and C16:0/C20:4 (m/z 782) in this decreasing intensity order in the positive ion mode, where Cn:m indicates an acyl group with n carbons and m double bonds in diacyl phosphatidylcholines. The results were consistent with those in the negative ion mode.

EXAMPLE 4

Figure 8:
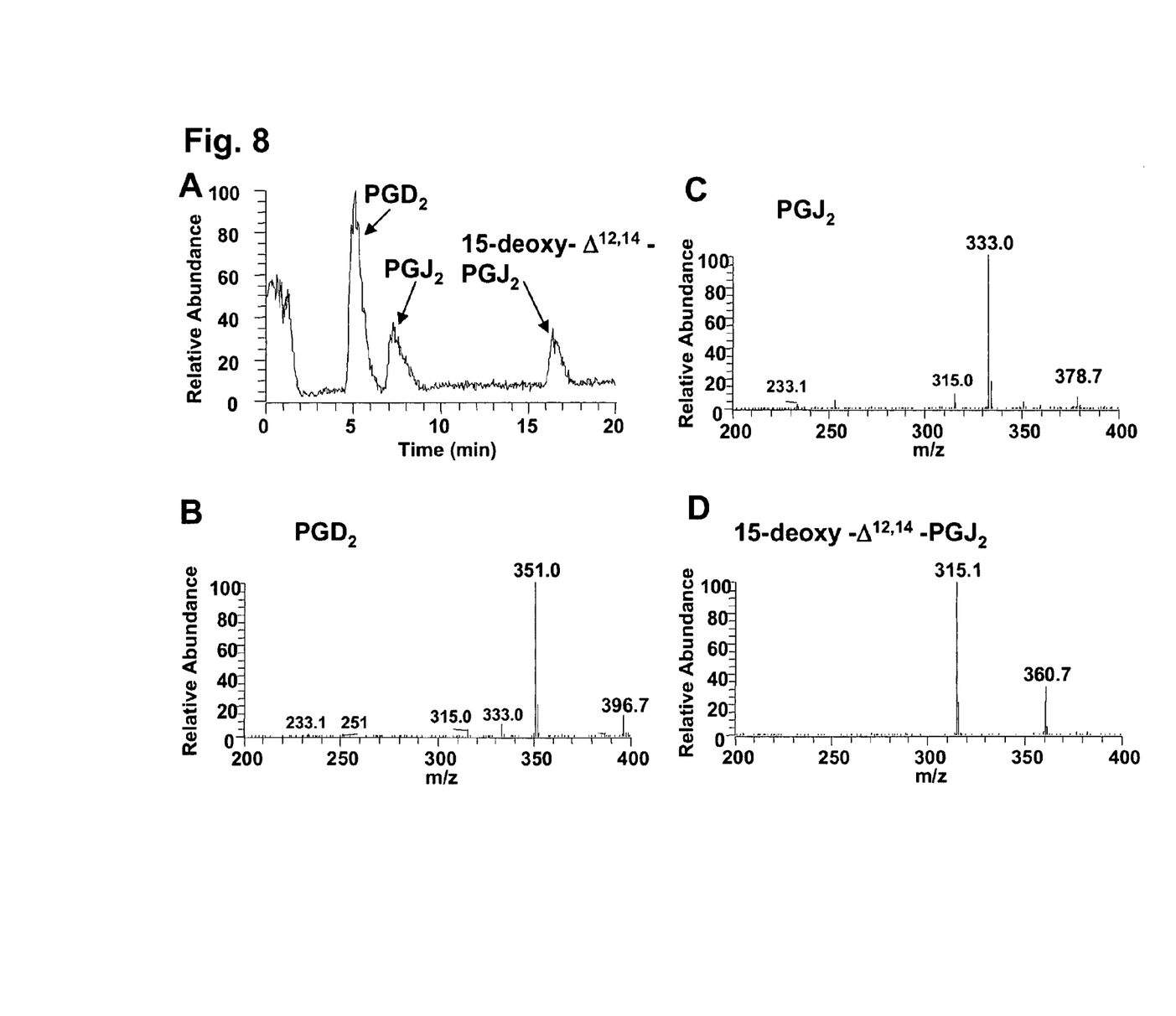
Figure 9:
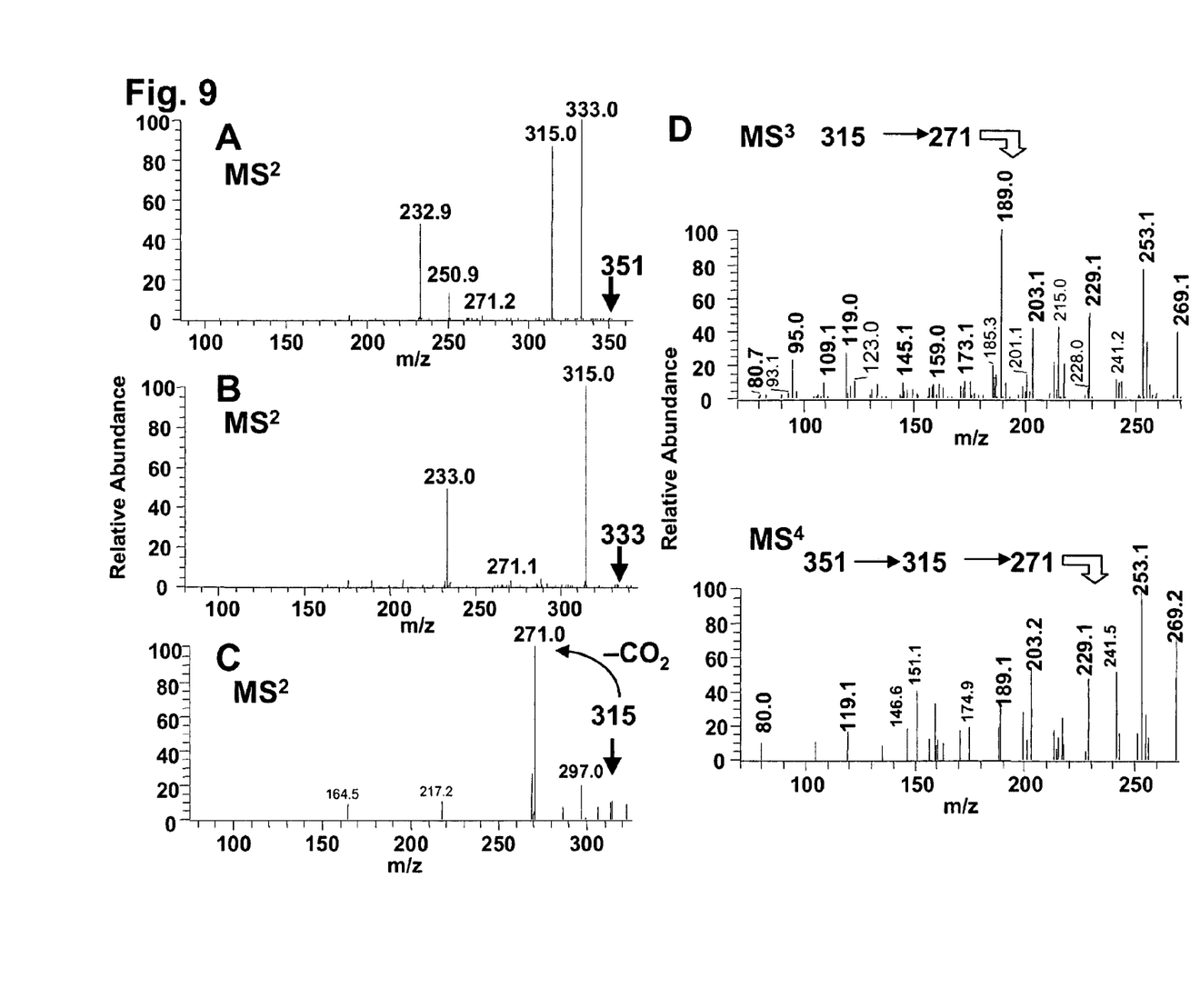
FIGS. 9A–C show on-line $MS^2$ product ion spectra of $PGD_2$, $PGJ_2$, and 15-deoxy-$\Delta^{12, 14}$-$PGJ_2$, respectively.
FIG. 9D shows $MS^3$ and $MS^4$ product ion spectra of 15-deoxy-$\Delta^{12, 14}$-$PGJ_2$ and $PGD_2$, respectively: the m/z 271 ions in 9C were fragmented on $MS^3$ scans (upper), and for $MS^4$ scans of $PGD_2$ carboxylate anions the m/z 351, 315, and 217 ions were sequentially selected (lower). For $MS^2$, $MS^3$, and $MS^4$ scans, relative collision energies of 32–40% were used.

To further examine the utility of the emitters in the negative ion mode using aqueous solvents, we analyzed the mixtures of prostaglandin $D_2$ ($PGD_2$) and its bioactive metabolites $PGJ_2$ and 15-deoxy-$\Delta^{12}$, $^{14}$-$PGJ_2$ by capillary reverse-phase HPLC on a Magic $C_{18}$ column (50×0.2 mm). The solvent systems used were the same as those for peptide separation as described above, but the column was pre-equilibrated with 15% solvent B and developed with a linear concentration gradient of solvent B from 15 to 30 in 1 min and from 30 to 45% in 20 min at the flow rate of ~1.5 μl/min. $PGJ_2$ and 15-deoxy-$\Delta^{12}$, $^{14}$-$PGJ_2$ are formed from $PGD_2$ by the elimination of one and two water molecules, respectively. Stable electrospray immediately occurred from water-rich, 15% solvent B, and last until the end of gradient (FIG. 8A). Full-scan spectra of these prostaglandins (0.5 pmol each) contain abundant deprotonated ions and minor formate-adduct ions. No signal derived from coating material was observed in the ESI mass spectra over the entire gradient range. The $MS_2$ product ion spectra of $[M-H]^{31}$ ions of $PGD_2$ and $PGJ_2$ contain abundant fragment ions generated by losses of one and two water molecules (m/z 333, and 315) and losses of water and hexanal formed by cleavage at the bond between $C^{14}$ and $C^{15}$ (m/z 233) (FIGS. 9A and B), consistent with the results of a previous study with fast atom bombardment MS (J. A. Zirrolli, J. Am. Soc. Mass Spectrom., 1, 325–335.). The neutral loss of $CO_2$ from the $[M-H]^-$ ions of 15-deoxy-$\Delta_{12}$, $^{14}$-$PGJ_2$ yielded abundant m/z 271 ions (J. A. Hankin, Arch. Biochem. Biophys., 340, 317–330) which underwent extensive fragmentation of the charge remote type on $MS^3$ scans with m/z 315, and 271 ions isolated sequentially for collision-induced dissociation (FIG. 9C). $MS^4$ scans gave the similar pattern with m/z 351, 315, and 271 ions isolated sequentially as precursor ions (FIG. 9D), confirming the fragmentation path of the carboxylate anions of $PGD_2$. These results indicate that the use of the emitters of this invention facilitates MS analyses in combination with HPLC and other separation methods in both proteomics and metabolomics.

This disclosure is provided to reveal a preferred embodiment of the invention and a best mode for practicing the invention. Having thus described the invention in this way, it should be apparent that various different modifications can be made to the preferred embodiment without departing from the scope and spirit of this disclosure. When structures are identified as a means to perform a function, the identification is intended to include all structures which can perform the function specified.

What is claimed is:

1. An electrospray emitter which comprises an emitter body comprising an inlet orifice, an outlet orifice and a channel connecting the inlet orifice and the outlet orifice; and a coating formed at least on the outer surface of the exit end of the emitter body with a material of low surface energy.

2. The electrospray emitter according to claim 1, wherein the material of low surface energy is a fluoropolymer or a fluorinated compound.

3. The electrospray emitter according to claim 2, wherein the fluoropolymer or the fluorinated compound is selected from perfluoropolyoxetane, perfluorourethane, fluoropolymer elastomers, polytetrafluoroethylene, fluoroalkyl monosilane, polymeric perfluoroether di- and poly-silane, and perfluorooctal and perfluoropolyether with an epoxy, hydroxy, acrylate or isocyanate functional group.

4. The electrospray emitter according to claim 1, wherein the material of low surface energy is perfluoropolyoxetane.

5. The electrospray emitter according to claim 4, wherein the outer wall and the inner wall of the emitter body are tapered toward the outlet orifice.

6. The electrospray emitter according to claim 1, wherein the coating is transparent or translucent.

7. The electrospray emitter according to claim 1, wherein the emitter body is made of fused-silica, glass ceramics, aluminosilicate glass, polypropyrene, or stainless steel.

8. The electrospray emitter according to claim 1, wherein the emitter body is tapered toward the outlet orifice.

9. The electrospray emitter according to claim 1, wherein the inner wall of the emitter body is also coated with the material of low surface energy according to claim 2.

10. The electrospray emitter according to claim 1, wherein the outlet orifice has an inner diameter of from 10 to 50 μm.

11. A method for making an electrospray emitter, which comprises: providing an electrospray emitter comprising an emitter body having an inlet orifice, an outlet orifice and a channel connecting the inlet orifice and the outlet orifice; and forming a coating with a material of low surface energy at least on the outer surface of the exit end of the emitter body.

12. A tubular connector for connecting an electrospray emitter and an analytical device, which comprises a tubular connector body comprising an inlet orifice, an outlet orifice and a passage communicating between the inlet orifice and the outlet orifice; and a coating formed on at least a portion of the inner surface of the connector body with a material with low surface energy.

13. The tubular connector according to claim 12, wherein the material of low surface energy is a fluoropolymer or a fluorinated compound.

14. The tubular connector according to claim 13, wherein the fluoropolymer or the fluorinated compound is selected from perfluoropolyoxetane, perfluorourethane, fluoropolymer elastomers, polytetrafluoroethylene, fluoroalkyl monosilane, polymeric perfluoroether di- and poly-silane, and perfluorooctal and perfluoropolyether with an epoxy, hydroxy, acrylate or isocyanate functional group.

15. The tubular connector according to claim 12, wherein the material of low surface energy is perfluoropolyoxetane.

* * * * *